United States Patent [19]

Sugisawa

[11] Patent Number: 4,493,708
[45] Date of Patent: Jan. 15, 1985

[54] INTRAVASCULAR CATHETER ASSEMBLY

[75] Inventor: Yasuhiko Sugisawa, Fujinomiya, Japan

[73] Assignee: Terumo Corporation, Tokyo, Japan

[21] Appl. No.: 420,814

[22] Filed: Sep. 21, 1982

[30] Foreign Application Priority Data

Dec. 10, 1981 [JP] Japan .......................... 56-182852[U]

[51] Int. Cl.³ ............................................ A61M 25/00
[52] U.S. Cl. ...................................... 604/165; 604/44
[58] Field of Search ..................... 604/43–45, 604/165, 283

[56] References Cited

U.S. PATENT DOCUMENTS

| 4,013,080 | 3/1977 | Froning | 604/165 |
| 4,037,599 | 7/1977 | Raulerson | 604/44 |
| 4,079,738 | 3/1978 | Dunn et al. | 604/165 |
| 4,256,119 | 3/1981 | Gauthier | 604/165 |
| 4,326,516 | 4/1982 | Schultz et al. | 604/165 |
| 4,405,312 | 9/1983 | Gross et al. | 604/283 |

FOREIGN PATENT DOCUMENTS 0000831 2/1979 European Pat. Off. .
55-119739 8/1980 Japan .

Primary Examiner—John D. Yasko
Assistant Examiner—Michelle N. Lester
Attorney, Agent, or Firm—Frishauf, Holtz, Goodman and Woodward

[57] ABSTRACT

An intravascular catheter or cannula assembly including a catheter device having a catheter tube and a catheter hub, and a cannula device having a cannula and a cannula hub. A cannula positioning rod is securely mounted on the cannula hub through a fixing member. A stopper is securely mounted on the catheter hub to abut against the distal end of the rod, thereby regulating the projecting length of the cannula from the distal end of the catheter tube when the cannula is inserted into the catheter tube. A member having a groove is provided to prevent an axial movement of the cannula. The groove tightly and detachably receives the fixing member and the stopper thereby integrally holding the catheter device and the cannula device when they are assembled.

15 Claims, 4 Drawing Figures

INTRAVASCULAR CATHETER ASSEMBLY

BACKGROUND OF THE INVENTION

I. Field of the Invention

The present invention relates to an intravascular catheter or cannula assembly which is dwelled in a vein of a patient to feed blood to an extracorporeal blood circuit or to inject an infusion solution into the vein.

II. Description of the Prior Art

An intravascular catheter generally comprises a catheter hub, and a flexible catheter tube which has an axial through hole and the proximal end of which is fixed to the hub. In order to insert the catheter into a vein, a cannula is first inserted through the through hole of the catheter tube from the proximal end side thereof such that the pointed end of the cannula may project slightly from the distal end of the catheter tube. Then, the projecting pointed end of the cannula is pierced into the vein, and the catheter tube is inserted into the vein by means of the cannula acting as a guide. After the catheter tube is inserted into the vein, the cannula is withdrawn from the catheter tube.

The length of the cannula which projects from the distal end of the catheter tube, when the cannula is inserted within the catheter tube, must be small and must remain constant. For this reason, various means have been proposed for regulating the length of the cannula portion which projects from the distal end of the catheter tube when the cannula is inserted within the catheter tube. One such means is disclosed, for example, in Japanese Utility Model Application Disclosure No. 55-119739 (its claim and drawings are laid open to public inspection on Aug. 25, 1980). The means of this application comprises a cannula positioning rod of a predetermined length, one end of which is fixed to the outer surface of a tubular hub mounted on a cannula and the other end of which extends toward the proximal end of a catheter, and a stopper which is mounted on a hub of the catheter to abut against the distal end of the cannula positioning rod. When the cannula is inserted into the catheter tube, the cannula positioning rod abuts against the stopper to receive it, thereby defining the projecting length of the cannula. With this cannula projecting length regulating means, the projecting length of the cannula may be easily regulated without requiring complex procedures such as rotation of the cannula.

However, when an assembly with the cannula projecting length regulating means as described above is assembled, and the pointed distal end of the cannula is pierced into the vein of a patient while the operator holds the catheter hub, the distal end of the cannula is sometimes withdrawn into the catheter tube and may not allow piercing due to the piercing resistance of the skin of the patient. This is because the cannula positioning rod is only in contact with the stopper in this state. If piercing is forcibly performed, not only the patient receives a strong pain but also the vein may be needlessly damaged or broken. In order to prevent this, it is necessary to pierce the cannula into the vein while preventing the withdrawal of the cannula by holding the catheter hub with the thumb and the forefinger and/or the middle finger and simultaneously holding the cannula hub with the medical finger and the small finger. However, when these measures are taken, the movement of the cannula may not be completely prevented, and the distal end of the cannula may still be withdrawn into the catheter tube upon an attempt to pierce the cannula into the vein is made. Particularly when the distal end of the cannula is withdrawn into the catheter tube during the piercing process, this might lead to a fatal problem. Furthermore, these measures are not suitable for an operator with small hands.

SUMMARY OF THE INVENTION

It is, therefore, an object of the present invention to provide an intravascular catheter or cannula assembly which is easy to handle for an operator with small hands and which may not cause withdrawal of the distal end of a cannula into a catheter tube even if the distal end of the cannula projecting from the catheter tube is pierced into a vein upon assembly the catheter with the cannula.

In order to achieve this object, there is provided according to the present invention an intravascular catheter or cannula assembly comprising:
catheter means including a catheter hub and a flexible catheter tube which has a longitudinal bore and a proximal end of which is fixed to said catheter hub;
cannula means including a hollow cannula body which is detachably inserted into said longitudinal bore and a distal end of which is arranged to project from a distal end of said catheter tube, and a cannula hub which supports said cannula body at a proximal end thereof;
means for regulating a length of the distal end of said cannula body projecting from the distal end of said catheter tube, said cannula projecting length regulating means including a cannula positioning rod, a proximal end of which is fixed on an outer surface of said cannula hub through a fixing member and a distal end of which projects parallel to said cannula body, and a rod stopper means which is mounted on an outer surface of said catheter hub to abut against a distal end of said cannula positioning rod, thereby regulating the length of the distal end of said cannula body projecting from the distal end of said catheter tube; and
means for preventing axial movement of said cannula means when said cannula body is inserted into said longitudinal bore of said catheter tube, said cannula axial movement preventing means having a groove which tightly detachably receives said fixing member and said rod stopper means.

A rigid connector is usually mounted, at its one end, to the proximal end of the catheter hub through a flexible connecting tube. A seal cap having an insertion hole for liquid-tightly receiving the cannula body is detachably and liquid-tightly mounted to the other end of the connector.

DETAILED DESCRIPTION OF THE PREFERRED EMBODIMENTS

Figure 1:
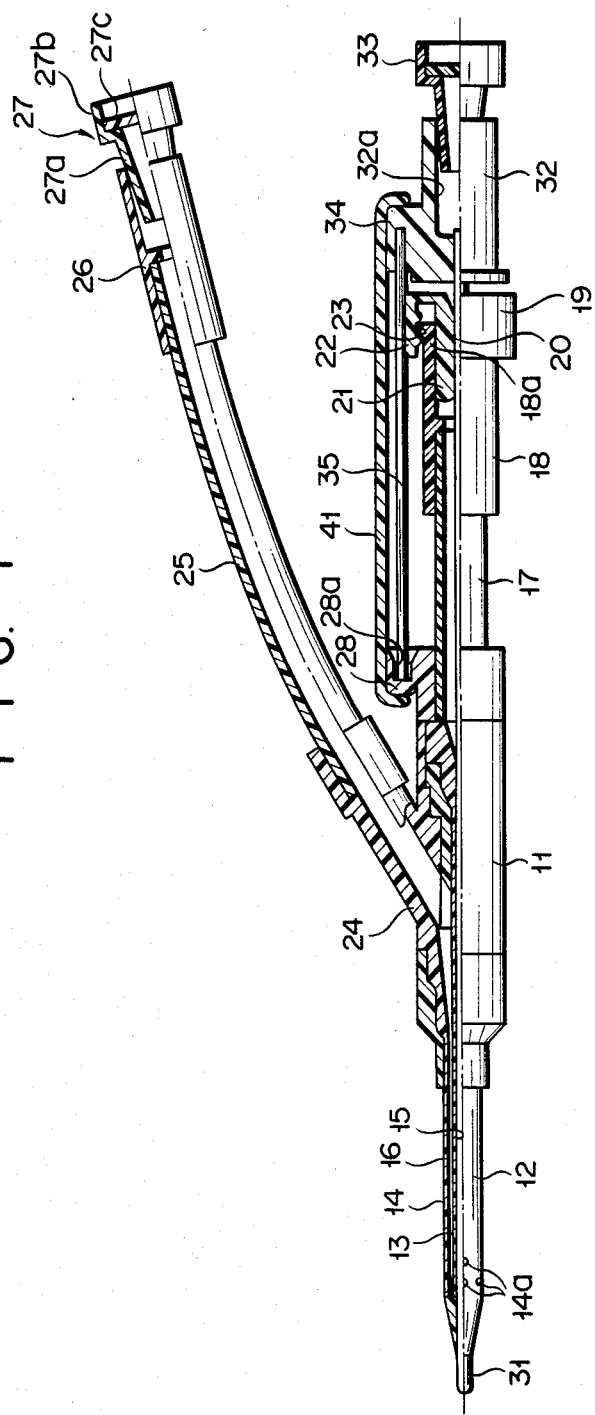
FIG. 1 is a partial sectional view of an intravascular catheter assembly according to the present invention.
Figure 2:
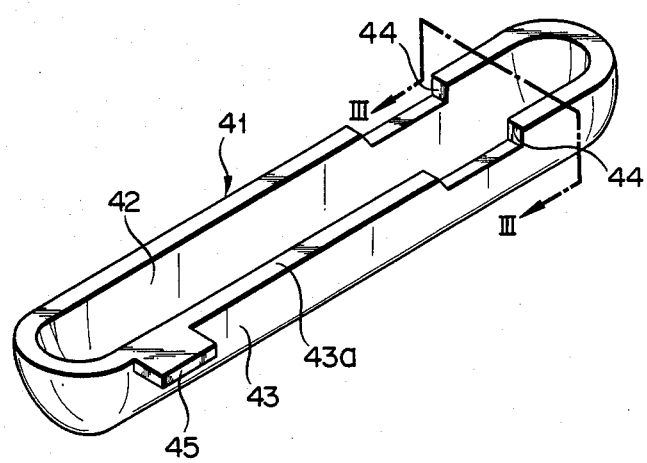
FIG. 2 is a perspective view of the cannula axial movement preventing member shown in FIG. 1.

FIG. 1 is a partial sectional view of an intravascular catheter assembly comprising a catheter section or device, a cannula section or device, and a cannula movement preventing member shown in FIG. 2. The catheter device has a hollow catheter hub 11 which is made of a transparent or semitransparent rigid resin such as polycarbonate or polypropylene, and a catheter tube 12 whose proximal end is fixed to the distal end of the hub 11 and which is made of a transparent or semitransparent flexible resin such as a fluorine resin.

The catheter tube 12 has a double structure of an inner tube 13 and an outer tube 14. The inner tube 13 defines therein an axial through (i.e., longitudinal bore 15) into which the cannula to be described later is inserted. The opposing walls of the inner and outer tubes 13 and 14 define an annular cavity 16 closed at its distal end. The hub 11 is fixed around the outer surface of the catheter tube 12. A plurality of small through holes 14a are formed at the distal end portion of the outer tube 14 of the catheter tube 12 to communicate the annular cavity 16 with the ambient atmosphere.

To the proximal end of the hub 11 is connected a transparent or semitransparent flexible connecting tube 17 of a relatively short length which is made of, for example, soft polyvinyl chloride and communicates with the through hole 15 of the catheter tube 12. To the proximal end of the connecting tube 17 is connected a connector 18 of a transparent or semitransparent rigid resin such as polycarbonate. A seal cap 19 is detachably connected to the proximal end of the connector 18. The seal cap 19 is made of, for example, a flexible or rigid polyvinyl chloride and has a tube 21 defining a small axial through hole 20 in which the cannula to be described later is liquid-tightly inserted therethrough. The inner wall of the through hole 20 tightly abuts against the outer wall of the cannula when the cannula is inserted therethrough. An annular flange 22 is formed integrally with the tube 21 to extend radially from the tube 21 and toward the distal end of the connector 18 parallel to the connector 18. A screw groove 23 is formed at that part of the inner wall of the flange 22 which extends parallel to the tube 21, and engages with a plurality of collars 18a formed on the part of the outer surface of the connector 18 at the proximal end thereof.

The catheter hub 11 has, at its intermediate position, a branch tube 24 which communicates with the annular cavity 16 of the catheter hub and which is made of a material same as that of the hub 11. A relatively long connecting tube 25 of a material same as that of the connecting tube 17 is fixed to the proximal end of the branch tube 24. A connector 26 similar to the connector 18 and preferably made of transparent or semi-transparent material is fixed around the part of the outer surface of the tube 25 at the proximal end thereof. To the proximal end of the connector 26 is mounted an air permeating cap 27 which includes a small diameter portion 27a detachably inserted into the connector 26 and a large diameter portion 27b connected to the small diameter portion 27a. An air permeating member 27c which allows permeation of air but does not allow permeation of blood therethrough is mounted within the large diameter portion 27b and across the through hole of the cap 27. The air permeating member 27c may be a membrane obtained by coating polyvinyl chloride on a polyester resin base, a membrane obtained by laminating polytetrafluoroethylene on polyethylene non-woven fabric, or a membrane obtained by coating silicone resin on an acetate film. The air permeating cap 27 may be entirely formed of a sintered body of a thermoplastic resin such as polyethylene, polypropylene or nylon, which is obtained by placing a powder of such a resin into a mold and compressing it under heating.

A rod stopper means 28 hereinafter referred to as ("stopper") is formed integrally with the part of the outer surface of the catheter hub 11 at the proximal end thereof. The stopper 28 has a recess 28a for receiving the distal end of the cannula positioning rod of the cannula device to be described below.

The cannula device comprises a cannula 31 to extend through the through hole 15 of the catheter tube 12 from the seal cap 19 of the catheter device and project from the distal end of the catheter tube 12, and a cannula hub 32 which supports the cannula 31 at the proximal end thereof. The cannula hub 32 has a recess 32a communicating with the inner hole of the cannula 31. An air permeating cap 33 similar to the cap 27 of the catheter device is inserted in the recess 32a.

A cannula positioning rod 35 of, for example, stainless steel is fixed, at its proximal end, to the part of the outer surface of the cannula hub 32 at the distal end thereof by a fixing member 34 securely mounted on the outer surface of the hub 32. The cannula positioning rod 35 extends parallel to the cannula 31 toward the distal end thereof past the seal cap 19. When the cannula 31 is inserted in the catheter, the distal end of the cannula positioning rod 34 enters inside the through hole 28a of the stopper 28 of the catheter hub 11, so that the length of the part of the cannula 31 which projects from the distal end of the catheter tube 12 is regulated to be constant.

A member 41 for preventing the axial movement or the withdrawal of the cannula 31 is incorporated in the assembly of the catheter device and the cannula device as shown in FIG. 1. As best shown in FIG. 2, the preventing member 41 is of substantially boat-like shape and has a groove 42 for tightly receiving the stopper 28 of the catheter device and the fixing member 34 of the cannula device. The movement preventing member 41 has a projection 45 for easy removal which is formed on that part of a side wall 43 which receives the stopper 28. The projection 45 is flush with a lower surface 43a of the side wall 43. Recesses 44 are formed within the lower surface 43a so that the seal cap 19 may not be brought into contact with the lower surface 43a of the side wall 43 when the preventing member 41 is mounted on the assembly.

Figure 3:
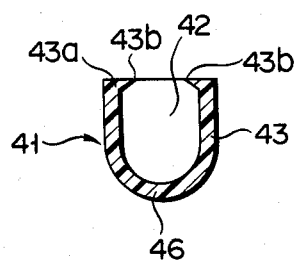
FIG. 3 is a sectional view along the line III—III in FIG. 2.
Figure 4:
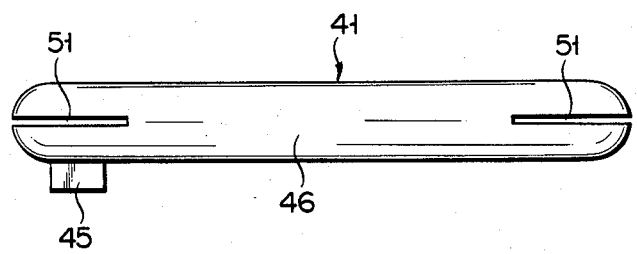
FIG. 4 is a plan view showing a modification of the cannula axial movement preventing means.

As shown in detail in FIG. 3, a relatively thin projection 43b projects inward from the lower surface 43a of the side wall 43 of the preventing member 41 so as to snap in the stopper 28 and the fixing member 34 in the groove 42 and to prevent dropout of the preventing member 41 after mounting. The preventing member 41 is made of a resin which has a slight elasticity such as polypropylene. If the preventing member 41 is made of a rigid resin which has substantially no elasticity such as polycarbonate, the member 41 preferably has, at least one end and preferably both ends of a bottom wall 46, a slit 51 extending in the longitudinal direction toward the center of the member 41, as shown in FIG. 4. The slit or slits 51 facilitate removal of the member 41.

When the intravascular catheter assembly of the present invention is assembled, the cannula 31 of the cannula device is first inserted within the through hole 15 of the catheter tube 12 from the seal cap 19 of the catheter device, and the cannula positioning rod 35 is locked by the stopper 28. Thus, the length of the projecting part of the cannula 31 from the catheter tube 12 is determined. Then, the movement preventing member 41 is mounted on the stopper 28 and the fixing member 34, and a protective tube (not shown) is mounted on the projecting distal end of the cannula 31 and the distal end of the catheter tube 12. The intravascular catheter assembly thus assembled is placed in a gas-permeable bag and sealed, sterilized by EOG (ethylene oxide gas) sterilization, and is directly provided to medical institutions.

When the intravascular catheter assembly thus assembled is used, the cannula is pierced into a vein while the catheter hub 11 alone is held by the operator without requiring removal of the preventing member 41. During this procedure, a piercing resistance of 400 to 600 g from the skin or the like acts on the distal end of the cannula 31. However, since the cannula device and the catheter device are securely fixed to each other by the movement preventing member 41, the distal end of the cannula 31 may not be withdrawn into the catheter tube 12. For this reason, effective piercing may be performed while holding the catheter hub 11 alone. When the distal end of the cannula 31 is pierced into the vein, blood flows into the cannula 31 owing to the air-permeability of the cap 33 and reaches the cannula hub 32. Since the hub 32 is transparent or semitransparent, flow-in of the blood, that is, piercing of the cannula 31 into the vein may be visually confirmed. After this is confirmed, the distal end of the catheter tube 12 is inserted together with the cannula 31 into the vein for a suitable length by using the cannula 31 as a guide such that the through holes 14a are inserted within the vein. Then, blood flows into the annular cavity 16 of the catheter from the through holes 14a formed near the distal end of the catheter tube 12 owing to the air-permeability of the cap 27, and then flows up to the cap 27. Since the catheter tube 12, the connecting tube 25 and/or the connector 26 is transparent or semitransparent, flow-in of blood into the catheter tube 12, the connecting tube 25 or the connector 26 may be confirmed visually. Then, flow-in of blood into the catheter tube 12 is confirmed. While the cannula hub 32 is held with one hand, the movement preventing member 41 is removed with the other hand by pressing the projection 45 with a finger to separate the cannula device from the catheter device. While the catheter hub 11 is held with one hand, the tip end of the cannula 31 is withdrawn to the position of the seal cap 19. Then, blood only flows to the intermediate position of the connecting tube 17. Subsequently, the connecting tubes 17 and 25 are closed by forceps, the cannula device is removed from the seal cap 19, and the seal cap 19 is removed. After adjusting the forceps such that no air remains within the connector 18, priming is performed, and the connector 18 is connected to one required terminal of a circuit such as a dialyzer. After the cap 27 is removed, the forceps are adjusted such that no air remains within the connector 26, and the connector 26 is connected to the other required terminal of the dialyzer.

As has been described above, the intravascular catheter assembly of the present invention is securely fixed by the movement preventing member 41 in the assembled state. Therefore, with the intravascular catheter assembly of the present invention, the cannula device and the catheter device remain integral with each other unless the movement preventing member 41 is removed. Accordingly, even if the cannula is pierced into a vein while the catheter hub 11 alone is held, the distal end of the cannula 31 may not be withdrawn into the catheter tube 12 due to the piercing resistance. Piercing into the vein is thus easy to accomplish without causing a great pain on the side of a patient or damage or breakage of the vein. The intravascular catheter assembly of the present invention easily allows piercing into the vein while the catheter hub 11 alone is held and also allows easy handling with an operator of small hands. With a conventional intravascular catheter assembly, the cannula must be pierced while holding both the cannula hub and the catheter hub so that the tip end of the cannula may not be withdrawn into the catheter tube. Unlike such a conventional intravascular catheter assembly, an intravascular catheter assembly of the present invention is easy to use.

As in the embodiment described above, if the movement preventing member 41 is formed in a boat shape elongating along the axial direction of the cannula positioning rod 35 so that it is detachable from the fixing member 34 and the stopper 28, the movement preventing member 41 may not interfere with the piercing of the cannula while the catheter hub 11 is held. Furthermore, when the movement preventing member 41 is to be removed from the fixing member 34 and the stopper 28 after the cannula 31 is pierced into the vein and dwells therein, the movement preventing member 41 and the catheter hub 11 or the cannula hub 32 may be held with both hands to remove the movement preventing member 41 without causing rotation of the pointed end of the cannula 31. The removal of the movement preventing member 41 is further facilitated by the projection 45 at one end of the member 41. Since the slit 51 of a predetermined length is formed at least at one end and preferably at both ends of the movement preventing member 41, removal of the member 41 is easy even if it is made of a rigid material which has lower elasticity. Since the movement preventing member 41 has the relatively thin projection 43b, the fixing member 34 and the stopper 28 snap in the groove 42 of the member 41 and is tightly surrounded by the inner wall of the groove 42. For this reason, the relative rotation between the cannula and catheter devices about the axial direction thereof is prevented, and the orientation of the pointed end of the cannula 31 projecting from the catheter tube may not be inadvertently rotated. Thus, the blood vessel is not damaged, and the holes 14a and the blade of the cannula 31 are set at prescribed positions, thereby lowering the piercing resistance during piercing operation of the cannula 31.

The present invention is not limited to a catheter of a double wall structure as described above. The present invention can be similarly applied to a catheter of a single tube type which does not have the branch tube and which has a single wall catheter tube.

What is claimed is:

1. An intravascular catheter or cannula assembly comprising:
   catheter means including a catheter hub and a flexible catheter tube which has a longitudinal bore and a proximal end of which is fixed to said catheter hub;
   cannula means including a hollow cannula body which is detachably inserted into said longitudinal bore and a distal end of which is arranged to project from a distal end of said catheter tube, and a cannula hub which supports said cannula body at a proximal end thereof;
   means for regulating a length of the distal end of said cannula body projecting from the distal end of said catheter tub, said cannula projecting length regulating means including a cannula positioning rod, a proximal end of which is fixed on an outer surface of said cannula hub through a fixing member and a distal end of which projects parallel to said cannula body and a rod stopper means which is mounted on an outer surface of said catheter hub to abut against a distal end of said cannula positioning rod, thereby regulating the length of the distal end of said cannula body projecting from the distal end of said catheter tube; and preventing means for preventing axial movement of said cannula means when said cannula body is inserted into said longitudinal bore of said catheter tube, said cannula axial movement preventing means having a side wall and a bottom wall defining a groove which tightly detachably receives said fixing member and said rod stopper means, said side wall and said botton wall extending along the axial direction of said cannula positioning rod, said side wall further having a first projection extending therefrom and a second thin projection which extends inwardly from an upper end of said side wall so as to snap in said fixing member and said rod stopper means into said groove.

2. An intravascular catheter or cannula assembly comprising:

catheter means including a catheter hub and a flexible catheter tube which has a longitudinal bore and a proximal end of which is fixed to said catheter hub;

cannula means including a hollow cannula body which is detachably inserted into said longitudinal bore and a distal end of which is arranged to project from a distal end of said catheter tube, and a cannula hub which supports said cannula body at a proximal end thereof;

means for regulating a length of the distal end of said cannula body projecting from the distal end of said catheter tub, said cannula projecting length regulating means including a cannula positioning rod, a proximal end of which is fixed on an outer surface of said cannula hub through a fixing member and a distal end of which projects parallel to said cannula body and a rod stopper means which is mounted on an outer surface of said catheter hub to abut against a distal end of said cannula positioning rod, thereby regulating the length of the distal end of said cannula body projecting from the distal end of said catheter tube; and preventing means for preventing axial movement of said cannula means when said cannula body is inserted into said longitudinal bore of said catheter tube, said cannula axial movement preventing means having a side wall and a bottom wall defining a groove which tightly detachably receives said fixing member and said rod stopper means, said side wall and said bottom wall extending along the axial direction of said cannula positioning rod, said side wall having a thin projection which extends inwardly from an upper end of said side wall so as to snap in said fixing member and said rod stopper means into said groove.

3. An assembly according to claim 1 or 2, further comprising a rigid connector fixed to a proximal end of said catheter hub through a flexible connecting tube.

4. An assembly according to claim 3, further comprising a seal cap which has an insertion hole into which said cannula body is inserted and which is detachably connected to a proximal end of said rigid connector.

5. An assembly according to claim 4, wherein said cannula hub has a recess at a proximal end thereof which communicates with the inner hole of said cannula body.

6. An assembly according to claim 5, wherein a member which permeates air and which does not permeate blood therethrough is provided at said recess of said cannula hub.

7. An assembly according to claim 1 or 2, wherein said preventing means is made of a resin which has elasticity.

8. An assembly according to claim 1 or 2, wherein said preventing means comprise a slit extending along the axial direction from at least one end toward a center thereof.

9. An assembly according to claim 8, wherein said preventing means is made of a rigid resin.

10. An assembly according to claim 1 or 2, wherein said catheter tube comprises a first tube member defining said longitudinal bore, and a second tube member defining with said first tube member an annular cavity closed at its distal end, at least one small through hole being formed at a distal end portion of said second tube member, and a proximal end of said annular cavity communicating with a branch tube connected to said catheter hub.

11. An assembly according to claim 10, wherein said catheter tube is transparent or semitransparent.

12. An assembly according to claim 11, wherein said connector is transparent or semitransparent.

13. An assembly according to claim 12, wherein said cannula hub is transparent or semitransparent.

14. An assembly according to claim 13, wherein said seal cap is made of a flexible resin and comprises an outer annular flange wall surrounding an outer surface of said connector, and a tube which projects along an axial direction of said outer annular flange wall and which has a small hole to tightly abut against an outer surface of said cannula body, an annular groove for receiving an opening port of said connector being formed between an inner surface of said outer annular flange wall and said tube.

15. An assembly according to claim 1 or 2, wherein said seal cap is made of flexible resin and comprises an outer annular flange wall surrounding an outer surface of said connector, and a tube which projects along an axial direction of said outer annular flange wall and which has a small hole to tightly abut against an outer surface of said cannula body, an annular groove for receiving an opening port of said connector being formed between an inner surface of said outer annular flange wall and said tube.

* * * * *